United States Patent [19]
Feingold et al.

[11] Patent Number: 6,162,229
[45] Date of Patent: *Dec. 19, 2000

[54] DEFORMABLE INTRAOCULAR LENS INJECTING APPARATUS WITH DEFORMABLE TIP PLUNGER

[75] Inventors: Vladimir Feingold, Laguna Niguel; Daniel C. Eagles, Capistrano Beach, both of Calif.

[73] Assignee: STAAR Surgical Company, Inc., Monrovia, Calif.

[ * ] Notice: This patent is subject to a terminal disclaimer.

[21] Appl. No.: 09/097,694

[22] Filed: Jun. 16, 1998

Related U.S. Application Data

[63] Continuation of application No. 08/570,564, Dec. 11, 1995, Pat. No. 5,772,666, and a continuation-in-part of application No. 08/547,908, Oct. 25, 1995, Pat. No. 5,616,148, and a continuation-in-part of application No. 08/449,103, May 24, 1995, abandoned, and a continuation-in-part of application No. 08/403,530, Mar. 14, 1995, abandoned, and a continuation-in-part of application No. 08/401,523, Mar. 10, 1995, Pat. No. 5,807,400, and a continuation-in-part of application No. 08/368,792, Jan. 4, 1995, and a continuation-in-part of application No. 08/345,360, Nov. 18, 1994, abandoned, and a continuation-in-part of application No. 08/197,604, Feb. 17, 1994, Pat. No. 5,499,987, and a continuation-in-part of application No. 08/196,855, Feb. 15, 1994, Pat. No. 5,941,886, and a continuation-in-part of application No. 07/953,251, Sep. 30, 1992, abandoned.

[51] Int. Cl.[7] ........................................ A61F 9/00
[52] U.S. Cl. ................................... 606/107; 623/6
[58] Field of Search .................................. 606/107; 623/6

[56] References Cited

U.S. PATENT DOCUMENTS

| 4,919,130 | 4/1990 | Stoy et al. ........................ 606/107 |
| 5,065,768 | 11/1991 | Coleman et al. ................. 606/107 |

*Primary Examiner*—Danton D. DeMille
*Assistant Examiner*—Benjamin Koo
*Attorney, Agent, or Firm*—Law Offices of William L. Klima, P.L.C.

[57] ABSTRACT

A deformable intraocular lens injecting apparatus having a movable plunger with a deformable plunger tip, preferably a resiliently deformable plunger tip. In a preferred embodiment, the plunger tip is made of soft resiliently deformable material to prevent any surface or internal damage to the deformable intraocular lens being forced through a delivery passageway of the lens injecting apparatus.

18 Claims, 7 Drawing Sheets

FIG. 28

DEFORMABLE INTRAOCULAR LENS INJECTING APPARATUS WITH DEFORMABLE TIP PLUNGER

RELATED APPLICATIONS

This application is a continuation of application Ser. No. 08/570,564, filed Dec. 11, 1995, now U.S. Pat. No. 5,772,666, and a continuation-in-part of U.S. patent application entitled "Transverse Hinged Deformable Intraocular Lens Injecting Apparatus", Ser. No. 08/547,908, filed Oct. 25, 1995, now U.S. Pat. No. 5,616,148; U.S. patent application entitled "Deformable Intraocular Lens Injection System, and Method Thereof", Ser. No. 08/449,103, filed May 24, 1995, now abandoned; U.S. patent application entitled "Deformable Intraocular Lens Injecting Device", Ser. No. 08/403,530, filed Mar. 14, 1995, now abandoned; U.S. patent application entitled "Deformable Intraocular Lens Insertion System", Ser. No. 08/401,523, filed Mar. 10, 1995, now U.S. Pat. No. 5,807,400; U.S. patent application entitled "Deformable Intraocular Lens Injection Systems And Methods Of Use Thereof", Ser. No. 08/368,792, filed Jan. 4, 1995, now pending; U.S. patent application entitled "Disposable Intraocular Lens Insertion System", Ser. No. 08/345,360, filed Nov. 18, 1994, now abandoned; U.S. patent application entitled "Deformable Intraocular Lens Cartridge", Ser. No. 08/197,604, filed Feb. 17, 1994, now U.S. Pat. No. 5,499,987; U.S. patent application entitled "Hingeless Lens Cartridges For Insertion Of Intraocular Lenses", Ser. No. 08/196,855, filed Feb. 15, 1994, now U.S. Pat. No. 5,941,886; and U.S. patent application entitled "Intraocular Lens Insertion System", Ser. No. 07/953,251, filed Sep. 30, 1992, now abandoned, all fully incorporated herein by reference.

FIELD OF THE INVENTION

The present invention is directed to a lens injecting apparatus including a deformable tip plunger for implantation of a deformable intraocular lens into the eye.

BACKGROUND OF THE INVENTION

Staar Surgical Company of Monrovia, Calif. produces deformable intraocular lens for implantation into the eye. These deformable intraocular lens are preferably implanted into the eye by use of a lens injecting apparatus. The lens injecting apparatus currently in use comprises two (2) separate components including 1) a lens injecting device including a cylindrical barrel having a lens cartridge receiver and a movable plunger disposed with the cylindrical barrel; and 2) a lens cartridge including a lens holding portion connected to a nozzle portion.

The movable plunger of the lens injecting device includes a tip for forcing a deformable intraocular lens loaded into the lens cartridge through a delivery passageway extending through the lens cartridge and out of the tip of the nozzle portion of the lens cartridge. Thus, when the tip of the nozzle portion is inserted through a small size incision made in the eye, the deformable intraocular lens exits the tip of the nozzle portion into the eye.

The movable plunger of the lens injecting device is slidable through an initial length of movement of the plunger, and then is threadedly advanced through a final length of movement of the plunger when forcing the deformable intraocular lens through the delivery passageway of the lens cartridge.

The lens injecting device including the plunger is made of titanium, plastic or stainless steel and the lens cartridge is made of plastic. The metal tip of the plunger has a fixed configuration. Specifically, the tip has a faceted configuration including a concave gripping surface portion and other surface portions defining the fixed geometry of the plunger tip.

SUMMARY OF THE INVENTION

A first object of the present invention is to provide a deformable intraocular lens injecting apparatus having a plunger with a deformable plunger tip.

A second object of the present invention is to provide a deformable intraocular lens injecting apparatus having a plunger with a compressible tip with a resiliently deformable plunger tip.

A third object of the present invention is to provide a deformable intraocular lens injecting apparatus having an inwardly tapering delivery passageway in the direction of insertion of the deformable intraocular lens and a plunger having a deformable plunger tip cooperating with the inwardly tapering passageway, and being compressed as advanced through the inwardly tapering passageway.

The present invention is directed to a lens injecting apparatus for implantation of a deformable intraocular lens into the eye. The lens injecting apparatus can have a one-piece construction (i.e., no lens cartridge) or can have a multi-piece construction including a separate lens injecting device having a lens cartridge receiver, and a separate lens cartridge.

The one-piece lens injecting apparatus includes a body portion having a lens delivery passageway extending therethrough and a movable plunger. The plunger can be slidably disposed within the delivery passageway, or the movement of the plunger can be limited such as by being threadedly advance through the delivery passageway. The one-piece lens injecting apparatus includes an opening or port for loading the deformable intraocular lens into the delivery passageway of the lens injecting apparatus.

The multi-piece lens injecting apparatus includes a separate lens injecting device having a lens cartridge receiver and a separate lens cartridge. The lens injecting device includes a passageway for accommodating a movable plunger. The passageway of the lens injecting device extends into a lens delivery passageway of the lens cartridge when the lens cartridge is loaded into the lens cartridge receiver of the lens injecting device.

The plunger used in the one-piece lens injecting apparatus or the multi-piece lens injecting apparatus is provided with a deformable tip. The deformable tip of the plunger is advantageous over a fixed configuration, since the deformable tip is made of deformable materials such as plastic, rubber, resin, foam, sponge, or other suitable material. These deformable materials are substantially softer materials compared with the fixed configuration tip of a metal or hard plastic plunger. Thus, the deformable tip plunger according to the present invention is substantially less likely to damage deformable intraocular lens, in particular delicate and thin deformable intraocular contact lenses (ICLs).

The deformable tip plunger according to the present invention can be made of a material having smaller dimensional size when dry and expandable to a larger dimensional size upon absorption of water or other suitable chemical. This would allow the plunger tip to be easily loaded and potentially stored in its smaller outer dimensional size, and then expand to its larger outer dimensional size mode upon contact with water or other suitable chemical (e.g. lubricating medium) at the time of use. For example, in the case of a deformable foam plunger tip contacting with water or balance salt solution during preparation of the lens injecting apparatus for use, the deformable foam plunger tip absorbs and increases its size, thus ensuring a tight fit with the inner walls of the cartridge delivery passageway. Further, the foam in this expanded condition is soft and highly pliable preventing any damage to the deformable intraocular lens.

In addition, the deformable tip plunger according to the present invention prevents the deformable intraocular lens or portions of the deformable intraocular lens, in particular the trailing haptic, from being caught between the plunger tip and inner wall of the delivery passageway when the plunger tip is being advanced forcing the deformable intraocular lens through the delivery passageway. Specifically, the deformable plunger tip can be sized to be slightly oversized compared to the inner dimensions of the delivery passageway so that the plunger tip is under slight compression when positioned within the delivery passageway. The radially outwardly directed compression force prevents the deformable intraocular lens or portion of the deformable intraocular lens from inadvertently moving or being forced between the exterior surface of the plunger tip and the inner wall surface of the delivery passageway.

In a preferred embodiment, the lens injecting apparatus is provided with an inwardly tapering delivery passageway in the direction of delivery of the deformable intraocular lens. Specifically, the cross-sectional size decreases in the direction of delivery to further fold, compress or otherwise reduce the cross-sectional size of the deformable intraocular lens as it is advanced through the delivery passageway. The deformable plunger tip according to the present invention is particularly suitable for an inwardly tapering delivery passageway, since the deformable plunger tip can be further and further compressed and reduced in outer dimensions as it is advanced through the inwardly tapering delivery passageway. This configuration allows the outer dimensions of the deformable plunger tip of the lens injecting apparatus to be further reduced to allow this tip to be inserted through a smaller sized incision in the eye.

DETAILED DESCRIPTION OF PREFERRED EMBODIMENTS

The present invention is directed to a lens injecting apparatus having a plunger with a deformable plunger tip. The deformable plunger tip allows the plunger tip to conform to the shape of the delivery passageway for the deformable intraocular lens through the lens injecting apparatus, in particular through an inwardly tapering passageway.

The deformable plunger tip is preferably resiliently deformable so that the deformable plunger tip can be deformed or compressed and then return to its original shape once the deformation or compression forces are removed. For example, the deformable plunger is made of elastomer (e.g., silicone), deformable plastic, deformable thermoplastic, rubber, foam, sponge, COLLAMER made by STAAR Surgical, or other suitable resiliently deformable material. A particularly suitable material for making the deformable tip according to the present invention is a surgical sponge material produced from cross-linked polyvinyl acetal (PVA) made by MEROCEL of Mistic, Conn. Further, when the resiliently deformable plunger tip is compressed, the plunger tip applies a wiping force between the outer surface of the plunger tip and the inner surface of the delivery passageway through the lens injecting apparatus. In this manner, a trailing haptic of the deformable intraocular lens cannot be caught between the plunger tip and delivery passageway when the plunger tip is forcing the deformable intraocular lens through the delivery passageway. When the deformable tip is made out of foam or spongy material, it can be smaller than the opening of the delivery passageway. When it comes into contact with water or balance salt solution, it expands and fills up completely the dimensions of the passageway.

The deformable plunger tip is preferably made of a soft resiliently deformable material to prevent any surface or internal damage to the deformable intraocular lens when the deformable plunger tip is being forced through the delivery passageway. For example, the deformable plunger tip can be made of essentially the same material as the particular deformable intraocular lens (e.g. silicone and COLLAMER made by STAAR Surgical Company).

The deformable plunger tip according to the present invention can be embodied in various lens injecting devices. For example, the present invention is applicable to a one-piece lens injecting device, which is a single piece once assembled, or a multi-piece lens injecting apparatus including a separate lens injecting device having a lens cartridge receiver, and a separate lens cartridge.

A preferred one-piece lens injecting apparatus 10 according to the present invention is shown in FIGS. 1–4.

The one-piece lens injecting apparatus 10 comprises 1) a body portion 12 having a lens receiver 14 for a deformable intraocular lens 15 and a lens delivery passageway 16 extending therethrough; and 2) a plunger 18 movably disposed within said body portion 12. The plunger 18 is provided with a plunger grip 20 and a deformable plunger tip 22.

In the one-piece lens injecting apparatus 10, the body portion 12 comprises a lens receiving portion 12a having a uniform cross-sectional sized and shaped delivery passageway portion 16a leading into a nozzle portion 12b having an inwardly tapering passageway portion 16b. The inner surfaces of the nozzle portion 16b defining the inwardly tapering delivery passageway portion 16b can be contoured (e.g., provided with ridges, grooves or other configuration) for folding and further folding the deformable intraocular lens 15 as it is forced through the inwardly tapering delivery passageway portion 16b by the deformable plunger tip 22.

The one end of the lens receiving portion 12a accommodates the plunger 18 to allow sliding movement of the plunger 18 inside the lens receiving portion 12a. Further, the nozzle portion 12b is provided with a nozzle tip 24 accommodating the exit end of the delivery passageway 16.

Figures 1, 2:
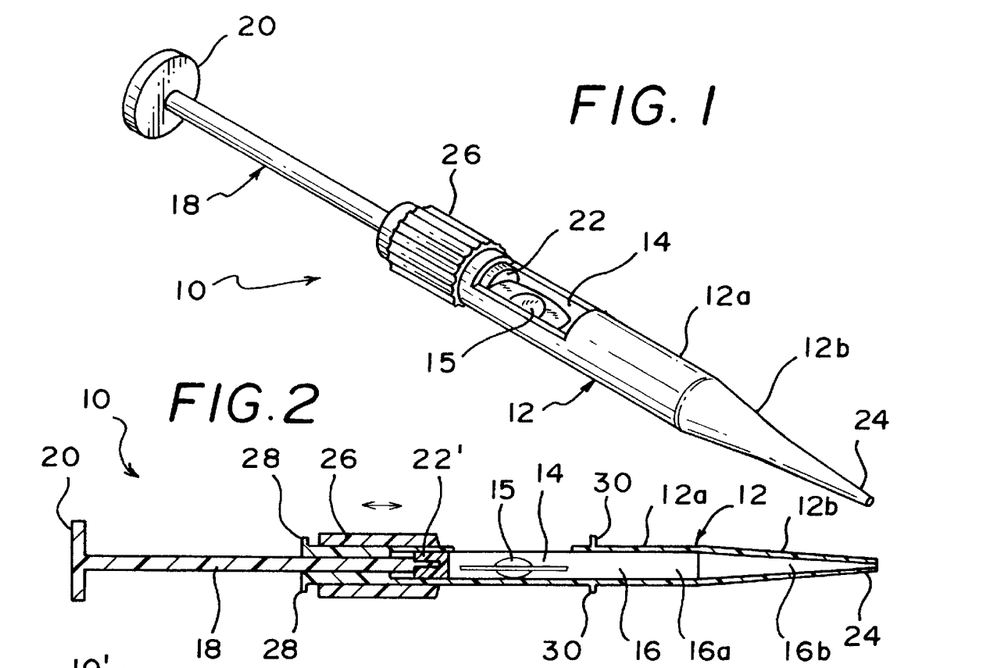
FIG. 1 is a perspective view of a preferred one-piece lens injecting apparatus with slidable cover for opening and closing the lens receiver opening, and having a deformable tip plunger according to the present invention.
FIG. 2 is a longitudinal cross-sectional view of the lens injecting apparatus shown in FIG. 1.

In this embodiment shown in FIGS. 1 and 2, the body portion 12 is provided with a slidable collar 26, which opens and closes the lens receiver 14 for loading or inspecting the deformable intraocular lens 15. The body portion 12 is also provided with two sets of stops 28 and 30 to limit movement of the slidable collar.

Figure 4:
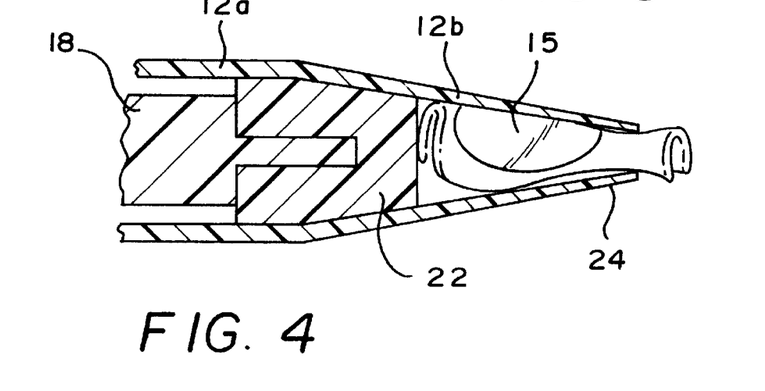
FIG. 4 is a broken away detailed longitudinal cross-sectional view of the nozzle portion of the lens injecting apparatus shown in FIGS. 1 and 2.

The deformable plunger tip 22 preferably has the same or similar cross-sectional size and shape as the delivery passageway 16. In a most preferred embodiment, the deformable plunger tip 22 is slightly oversized compared with the inner dimensions of the delivery passageway portion 16a so that the deformable plunger tip 22 is under a slight compression to prevent a trailing haptic of the deformable intraocular lens 15 from moving in between the outer surface of the deformable plunger tip 22 and the inner surface of the delivery passageway portion 16a. When the deformable plunger tip 22 reaches the inwardly tapering delivery passageway portion 16b, the deformable plunger tip 22 is further and further compressed and its outer surface tapers inwardly and conforms to the inwardly tapering delivery passageway portion 16b, as shown in FIG. 4.

As the deformable plunger tip 22 is further compressed, the compression stress at the interface between the outer surface of the deformable plunger tip 22 and inner surface of the delivery passageway portion 16b significantly increases making it more difficult for the trailing haptic of the deformable intraocular lens 15 from moving in between the outer surface of the deformable plunger tip 22 and the inner surface of the delivery passageway portion 16a. This increased compression at the interface between the outer surface of the deformable plunger tip 22 and the inner surface of the delivery passageway portion 16b is necessary to counteract the increasing compression stresses on the deformable intraocular lens causing the deformable intraocular lens to move towards and seek any void space or weak wall surface inside the delivery passageway (i.e., in particular, any space between the outer edge of the deformable plunger tip 22 and the inner surface of the delivery passageway portion 16b). Thus, the deformable intraocular lens 15 will continue to advance forward while being further compressed as it moves towards and exits the nozzle tip 24.

In a most preferred embodiment, the deformable plunger tip 22 also has the same cross-sectional shape (e.g., oval, round, curved, contoured, grooved) as the cross-sectional shape of the delivery passageway 16, again to prevent a trailing haptic of the deformable intraocular lens 15 from moving in between the outer surface of the deformable plunger tip 22 and the inner surface of the delivery passageway 16.

In another most preferred embodiment, the deformable plunger tip 22 is made of an expandable material (e.g. foam). More specifically the deformable plunger tip 22 is made of a material that expands within the delivery passageway 16 upon contact with water or balanced saline solution. This type of deformable plunger tip 22 is very soft and highly pliable preventing any damage to the deformable intraocular lens. Further, the expansion of the material prevents the trailing haptic from getting caught between the deformable plunger tip 22 and the inner wall of the delivery passageway 16.

In operation, the slidable collar 26 is slid to the left to open the lens receiver 14. The deformable intraocular lens 15 is then loaded in a flat configuration into the lens receiver 14 of the lens injecting apparatus 10. The slidable collar 26 in then slid to the right to close the lens receiver 14. The user exerts a force on the grip 20 with his or her fingers or thumb causing the plunger 18 to slide forward into contact with the deformable intraocular lens 15. The user continues to advance the plunger 18 so that the deformable intraocular lens 15 is moved through the delivery passageway portion 16a in a flat unstressed configuration and into the delivery passageway portion 16b to cause the lens to be folded and/or compressed.

The lens injecting apparatus is now loaded, and readied for lens insertion. The user then inserts the tip of the nozzle tip 24 through a small incision in the eye, and then advances the plunger 18 so that the deformable intraocular lens 15 is folded or compressed as it passes through the inwardly tapering passageway portion 16b until it exits from the nozzle tip 24 inside the eye.

The lens injecting apparatus 10 can be preloaded with the deformable intraocular lens 15 so that a user can slid the slidable collar to the left to open the lens receiver 14' to inspect the deformable intraocular lens 15, and then slid to the right to close the lens receiver 14.

Figure 3:
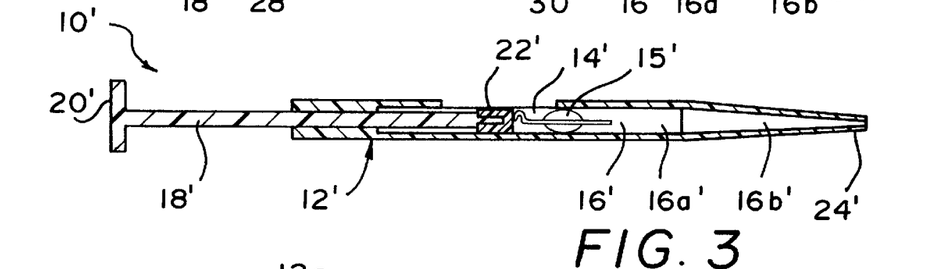
FIG. 3 is another preferred embodiment of the one-piece lens injecting apparatus similar to the one shown in FIGS. 1 and 2, however, with no slidable cover.

A further preferred embodiment of a one-piece lens injecting apparatus 10', is shown in FIG. 3. In this embodiment, the body portion 12' is not provided with a slidable collar 26 as in the embodiment shown in FIGS. 1 and 2. Instead, the lens receiver 14 is opened until the plunger tip 22' is advanced sufficiently forward to close off the opening into the delivery passageway 16.

In operation, the deformable intraocular lens 15' is loaded in a flat configuration into the lens receiver 14' of the lens injecting apparatus 10'. The user exerts a force on the grip 20' with his or her fingers or thumb causing the plunger 18' to slide forward into contact with the deformable intraocular lens 15'. The user continues to advance the plunger 18' so that the deformable intraocular lens 15' is moved through the delivery passageway portion 16a' in a flat unstressed configuration.

The lens injecting apparatus is now loaded, and readied for lens insertion. The user then inserts the tip of the nozzle tip 24' through a small incision in the eye, and then advances the plunger 18' so that the deformable intraocular lens 15' is folded or compressed as it passes through the inwardly tapering passageway portion 16b' until it exits from the nozzle tip 24' inside the eye.

Deformable Plunger Tip Designs

A variety of deformable plunger tips designs are shown in FIGS. 5–17. The plungers 18 are shown as being made of plastic, however, the plungers 18 can be made of metal, ceramic or other suitable material having sufficient structural strength and properties for proper operation thereof.

The deformable plunger tips can be made to be deformable by 1) using a deformable material, preferably a resiliently deformable material; 2) using a configuration that allows deformation (e.g. hollow tip); or 3) both methods of 1 & 2; and/or 4) using a foam or sponge material so that the plunger tip absorbs water and swells to a larger size, thus, the expanded nature of the foam or sponge material is deformable. The deformable plunger tips are preferably made of resiliently deformable materials, since these materials tend to have "soft" surface properties that prevent damage to the deformable intraocular lenses during delivery.

Figure 5:
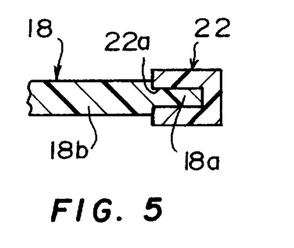
FIG. 5 is a detailed view of a first preferred embodiment of a plunger tip according to the present invention.

In FIG. 5, the deformable plunger tip 22 is provided on an end of the plunger 18. More specifically, the deformable plunger tip 22 is provided with a recess 22a for accommodating an end portion 18a having a reduced cross-sectional size compared with a main portion 18b of the plunger 18. The cross-sectional size of the recess 22a can be made slightly smaller than the cross-sectional size of the end portion 18a of the plunger 18 to provide an interference type fit. Alternatively, or in addition, adhesive, welding, or other type of bonding can be provided between the deformable plunger tip 22 and plunger 18.

Figure 6:
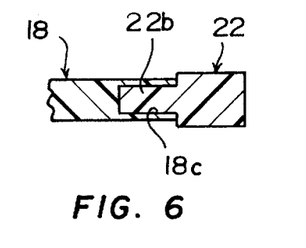
FIG. 6 is a detailed view of a second preferred embodiment of a plunger tip according to the present invention.

In FIG. 6, the deformable plunger tip 22 is provided with a protrusion 22b received within a recess 18c in an end face of the plunger 18. The outer dimensions of the protrusion 22b can be made to be slightly larger than the inner dimensions of the recess 18c of the plunger 18 to provide an interference fit. Alternatively, or in addition, adhesive, welding, or other type of bonding can be provided between the deformable plunger tip 22 and plunger 18.

Figure 7:
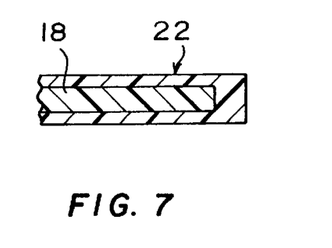
FIG. 7 is a detailed view of a third preferred embodiment of a plunger tip according to the present invention.

In FIG. 7, a substantial portion or the entire plunger 18 is coated with the deformable plunger tip 22. For example, a silicone resin is molded around a more stiff plastic plunger 18.

Figure 8:
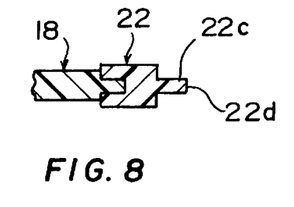
FIG. 8 is a detailed view of a fourth preferred embodiment of a plunger tip according to the present invention.

In FIG. 8, the deformable plunger tip 22 is provided with a protrusion 22c to provide a side clearance between the deformable plunger tip 22 and the delivery passageway to accommodate a trailing haptic, in particular the trailing haptic of a three (3) piece type deformable intraocular lens. The end face 22d contacts the optic of the deformable intraocular lens.

Figure 9:
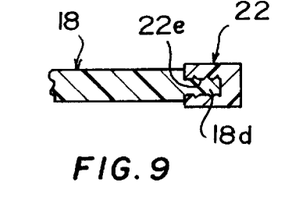
FIG. 9 is a detailed view of a fifth preferred embodiment of a plunger tip according to the present invention.

In FIG. 9, the plunger 18 is provided with a threaded or barbed end portion 18d to enhance gripping with the deformable plunger tip 22. The recess 22e may also be threaded or barbed to further enhance gripping.

Figure 10:
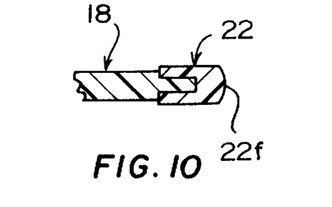
FIG. 10 is a detailed view of a sixth preferred embodiment of a plunger tip according to the present invention.

In FIG. 10, the deformable plunger tip 22 is provided with a convex tip 22f.

Figure 11:
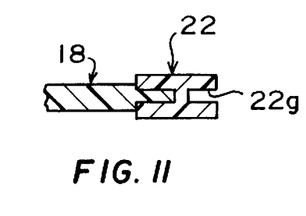
FIG. 11 is a detailed view of a seventh preferred embodiment of a plunger tip according to the present invention.

In FIG. 11, the deformable plunger tip 22 is provided with a slotted tip 22g to accommodate the trailing haptic of a plate type or three (3) piece type deformable intraocular lens.

Figure 12:
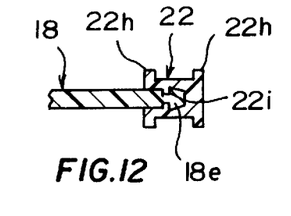
FIG. 12 is a detailed view of an eighth preferred embodiment of a plunger tip according to the present invention.

In FIG. 12, the deformable plunger tip 22 is provided with a set of wipers 22h to concentrate stress between the wipers and inner surface of the delivery passageway to prevent the trailing haptic of the deformable intraocular lens from getting caught in between the deformable plunger tip 22 and the inner surface of the delivery passageway. Alternatively, a single wiper or additional wipers can be provided. In addition, the plunger 18 is provided with a barbed end 18e to enhance gripping. Further, a recess in the deformable plunger tip can be provided with a ridge 22i to cooperated with the barbed end 18e to further enhance gripping.

Figure 13:
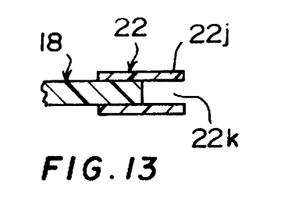
FIG. 13 is a detailed view of a ninth preferred embodiment of a plunger tip according to the present invention.

In FIG. 13, a section of tubing 22j can be provided on the end of the plunger 18 to function as a deformable plunger tip 22. For example, a section of soft polyurethane or silicone tubing is suitable. The section of tubing 22j can be attached by stretching due to its elastic resiliency (i.e. stretched fit), and/or attached with adhesive or bonding. The inner passageway 22k in the tubing 22j can accommodate the trailing haptic of the deformable intraocular lens. Further, the configuration of the section of tubing 22i having a void space inside provided by the inner passageway 22k enhances the deformability of the deformable plunger tip 22 (i.e., will deform inwardly with less compressive stress compared to solid type tip).

Figure 14:
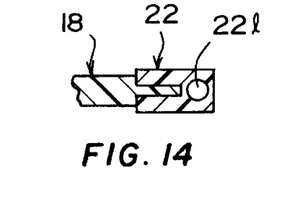
FIG. 14 is a detailed view of a tenth preferred embodiment of a plunger tip according to the present invention.

In FIG. 14. the deformable plunger tip 22 is provided with a void space 22l to enhance the deformability of the deformable plunger tip 22 (i.e., will deform inwardly with less compressive stress compared to solid type tip while still maintaining more resistance to compression at end face thereof). The void space 22l is shown as being round, however, other configurations such as rectangular, curved, multiple voids (e.g., foam or sponge) can be substituted.

Figure 15:
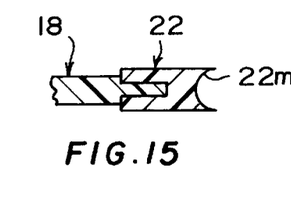
FIG. 15 is a detailed view of an eleventh preferred embodiment of a plunger tip according to the present invention.

In FIG. 15, the deformable plunger tip 22 is provided with a concave end face 22m for capturing the trailing haptic of the deformable intraocular lens near the centerline of the delivery passageway, and maintaining the trailing haptic away from the inner walls of the delivery passageway.

Figure 16:
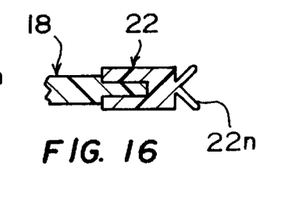
FIG. 16 is a detailed view of a twelfth preferred embodiment of a plunger tip according to the present invention.

In FIG. 16, the deformable plunger tip 22 is provided with a scraper 22n for capturing the trailing haptic of the deformable intraocular lens near the centerline of the delivery passageway, and maintaining the trailing haptic away from the inner walls of the delivery passageway. Further, the scraper can deform inwardly under compressive force and apply a scraping spring force against the inner wall of the delivery passageway due to its cantilever configuration. The scraper 22n can have a cone shape, or be made of separate paddles.

Figure 17A:
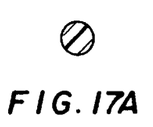
FIG. 17A is a transverse cross-sectional view of a circular shaped plunger tip according to the present invention.
Figure 17B:
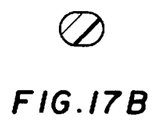
FIG. 17B is a transverse cross-sectional view of an oval shaped plunger tip according to the present invention.

In FIGS. 17A to 17B, various transverse cross-sectional shapes of the deformable plunger tip are shown. The transverse cross-sectional shape of the plunger tip can remain fixed throughout its length or its transverse cross-sectional shape can vary along its length.

Figure 17C:
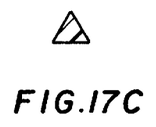
FIG. 17C is a transverse cross-sectional view of a triangular shaped plunger tip according to the present invention.
Figure 17D:
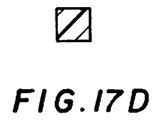
FIG. 17D is a transverse cross-sectional view of a square shaped plunger tip according to the present invention.
Figure 17E:
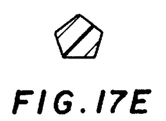
FIG. 17E is a transverse cross-sectional view of a pentagonal shaped plunger tip according to the present invention.
Figure 17F:
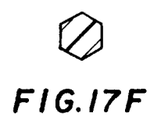
FIG. 17F is a transverse cross-sectional view of a hexagonal shaped plunger tip according to the present invention.
Figure 17G:
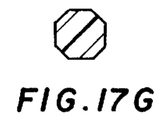
FIG. 17G is a transverse cross-sectional view of an octagonal shaped plunger tip according to the present invention.

A deformable plunger tip 22o having a circular transverse cross-sectional shape is shown in FIG. 17A. A deformable plunger tip 22p having an oval transverse cross-sectional shape is shown in FIG. 17B. A deformable plunger tip 22q having a triangular transverse cross-sectional shape is shown in FIG. 17C. A deformable plunger tip 22r having a rectangular (e.g. square) transverse cross-sectional shape is shown in FIG. 17D. A deformable plunger tip 22s having a pentagonal transverse cross-sectional shape is shown in FIG. 17E. A deformable plunger tip 22t having a hexagonal transverse cross-sectional shape is shown in FIG. 17F. A deformable plunger tip 22u having an octagonal transverse cross-sectional shape is shown in FIG. 17G.

Multi-Piece Lens Injecting Apparatus

A multi-piece lens injecting apparatus 100 according to the present invention is shown in FIGS. 18–26.

The multi-piece lens injecting apparatus 100 comprises a separate lens injecting device 102 and a separate lens cartridge 104. The lens injecting device 102 comprises a body portion 106 having a lens cartridge receiver 108 and an internally threaded end portion 110. A movable plunger 112 is disposed within the body portion 106.

Figures 21, 22:
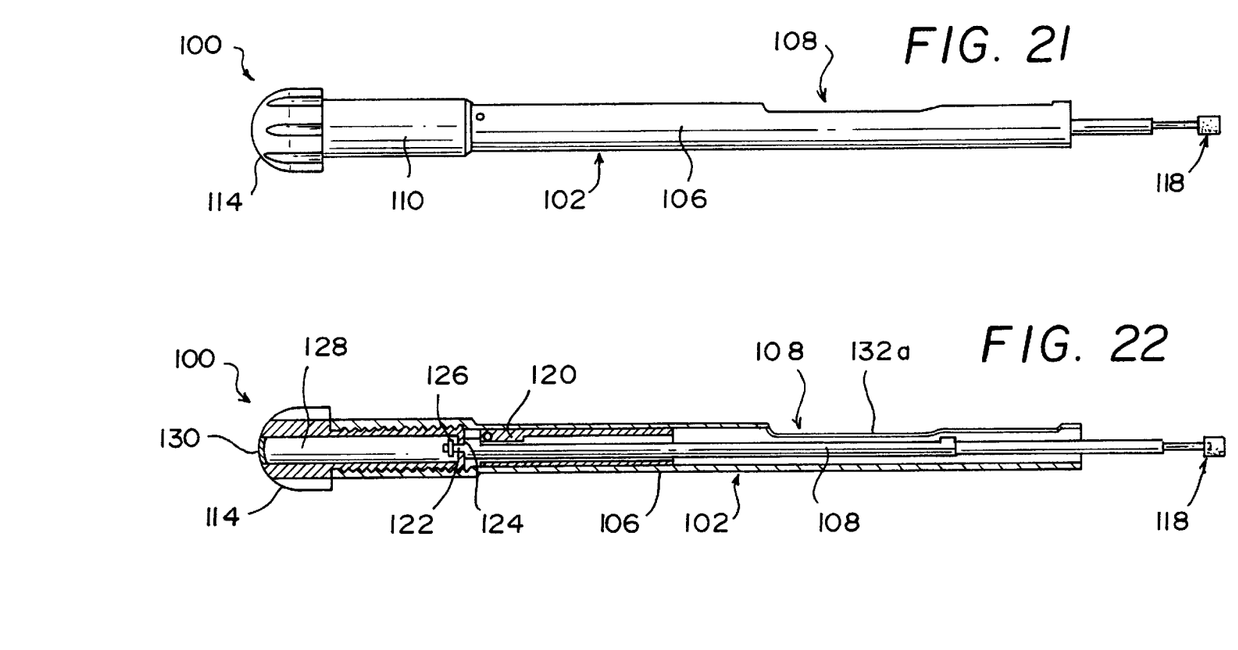
FIG. 21 is a side elevational view of the preferred multi-piece lens injecting apparatus shown in FIG. 17.
FIG. 22 is a longitudinal cross-sectional view of the preferred multi-piece lens injecting apparatus shown in FIG. 17.

The movable plunger 112 is provided with a grip 114 having an externally threaded portion 116 at one end, and a plunger tip 118 at an opposite end (See FIG. 22) thereof. The plunger 112 is slidably disposed within the body portion 106. Specifically, the body portion 106 is provided with an internally fitted guide 120, as shown in FIG. 22, for slidably supporting the plunger 112 within the body portion 106. In operation, the plunger 112 is advanced by sliding the plunger within the body portion 106 an initial distance until the externally threaded portion 116 of the grip 114 engages with the internally threaded portion 110 of the body portion 106. Then, the grip 114 is rotated to threadedly advance the plunger 112 in a very accurate and controlled manner through a final distance causing the deformable intraocular lens to move through and out of the lens cartridge into the eye.

The plunger 112 is provided with a threaded extension 122 passing through a hole in the end face 124 of the externally threaded end portion 116 of the grip 114, as shown in FIG. 22. A nut 126 is located inside a passageway 128 of the grip 114 and fastened onto the threaded extension 122 to connect the grip 114 to the end of the plunger 112. An end cap 130 is provided to seal the end of the passageway 128 in the grip 114.

Figures 18, 19:
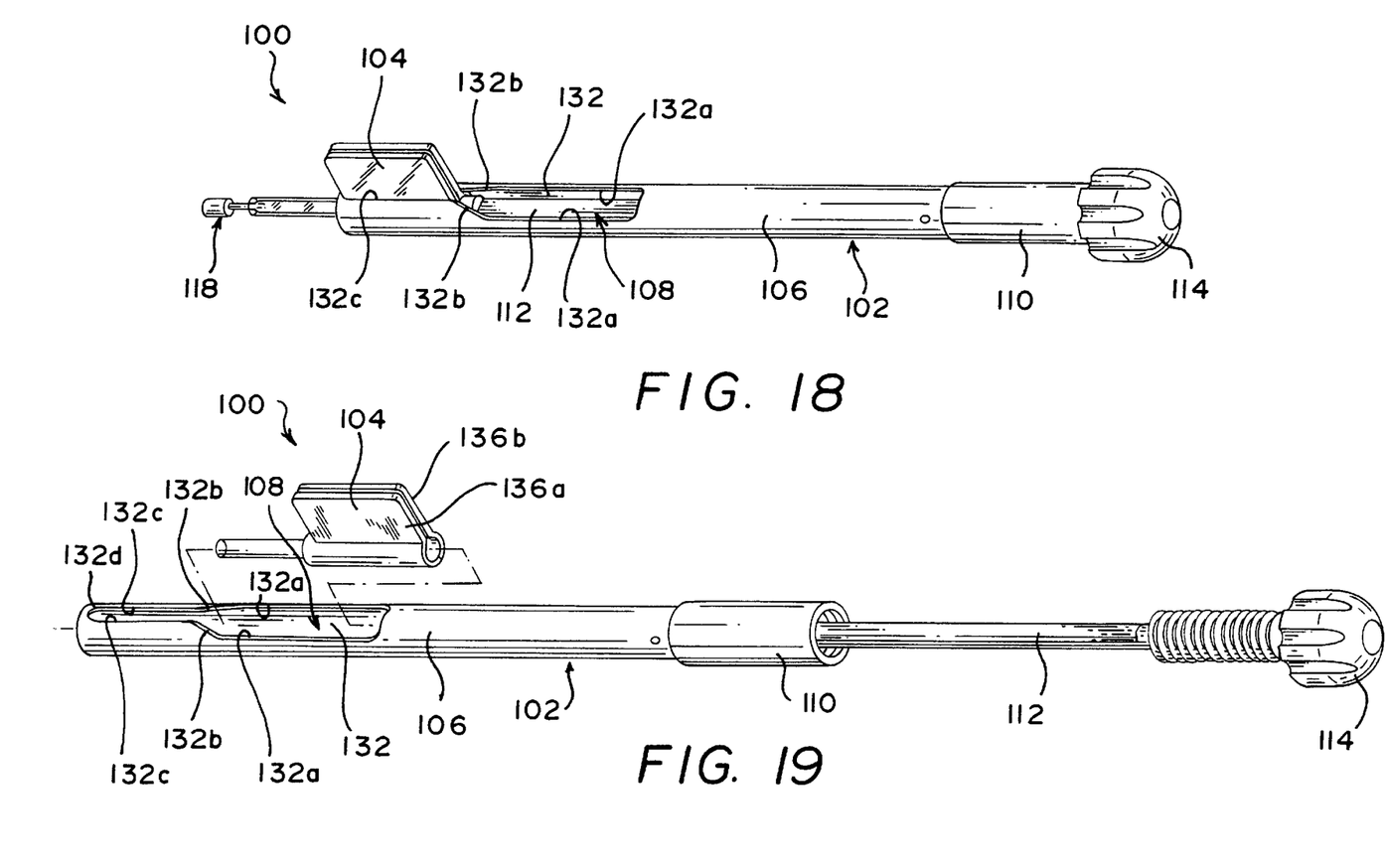
FIG. 18 is a perspective view of a preferred multi-piece lens injecting apparatus having a deformable tip plunger according to the present invention.
FIG. 19 is another perspective view of the preferred multi-piece lens injecting apparatus shown in FIG. 17 having a deformable tip plunger according to the present invention.
Figure 20:
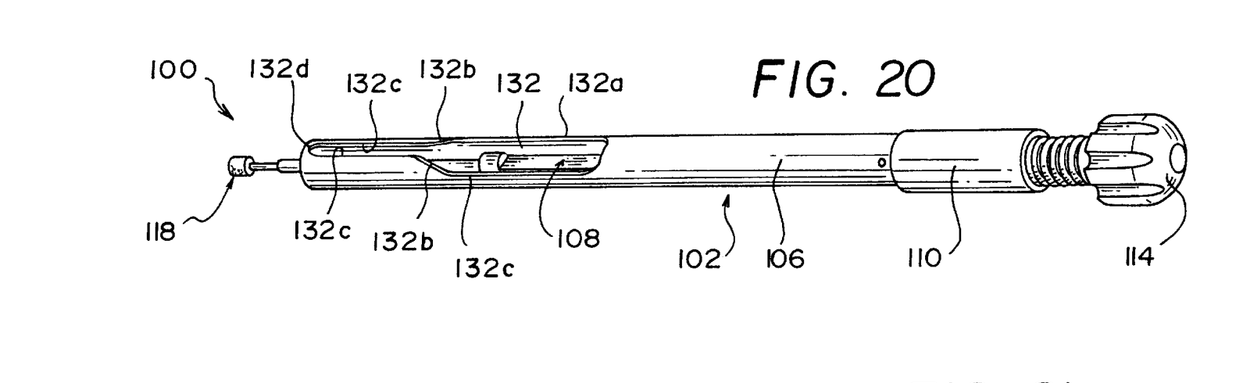
FIG. 20 is a further perspective view of the preferred multi-piece lens injecting apparatus shown in FIG. 17 having a deformable tip plunger according to the present invention.

The lens cartridge receiver 108 of the body portion 106 is provided by an opening 132 in the side of the body portion 106. The opening 132 is defined by a set of wider spaced apart parallel edges 132a, a set of inwardly tapering edges 132b, a set of thinner spaced apart parallel edges 132c, and a stop edge 132d. The lens cartridge 104 is loaded in lens injecting device 102 through the opening 132 between the set of wider spaced apart parallel edges 132a of the lens cartridge receiver 108. Then the lens cartridge 104 is moved forward within the lens cartridge receiver 108.

The plunger tip 118 is made of a deformable material, preferable a resilient deformable material such as plastic, rubber, foam, sponge or other suitable material. The remaining parts of the lens injecting device can be made of structural grade plastic (e.g., polysulfone) or metal (e.g., stainless steel or titanium) allowing autoclaving thereof.

Figure 23:
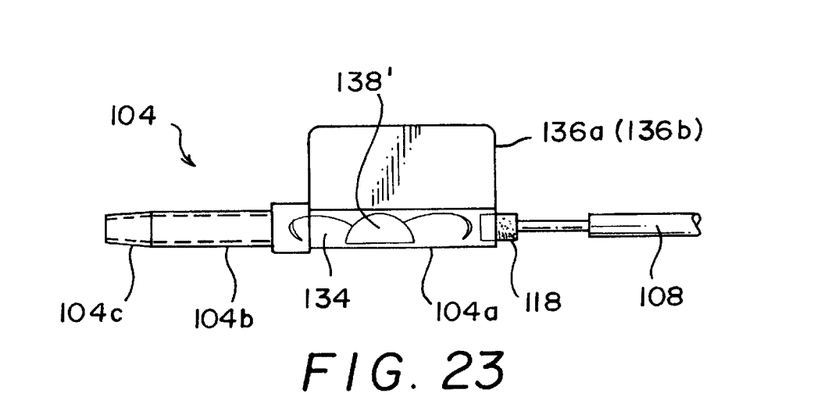
FIG. 23 is a side elevational view of a lens cartridge showing the plunger tip according to the present invention entering one end of the delivery passageway through the lens cartridge.

The lens cartridge 104 is preferably made of plastic (e.g., polypropylene, polysulfone, Neoflon, polyethylene and silicone), and has a foldable design, as shown in FIG. 18. As shown in FIG. 23, the lens cartridge 104 includes a lens holding portion 104a connected to a nozzle portion 104b having a nozzle tip 104c. A delivery passageway 134 extends throughout the length of the lens cartridge 104. The lens cartridge further includes a pair of extensions 136a and 136b for opening and closing the lens cartridge 104. Further, the extensions 136a and 136b cooperate with the edges 132a, 132b and 132c of the opening 132 of the lens cartridge receiver 108.

In operation, the lens cartridge 104 is loaded with a deformable intraocular lens and a viscoelastic lubricant. The lens cartridge 104 is then loaded into the lens cartridge receiver 108 of the lens injecting device 102. Specifically, the lens cartridge is inserted through the opening 132 of the lens cartridge receiver 108 and then moved forward so that the extensions are squeezed together by the set of inwardly tapering edges 132b and the set of thinner parallel set apart edges 132c until the extensions reach the edge stop 132d.

Figure 24:
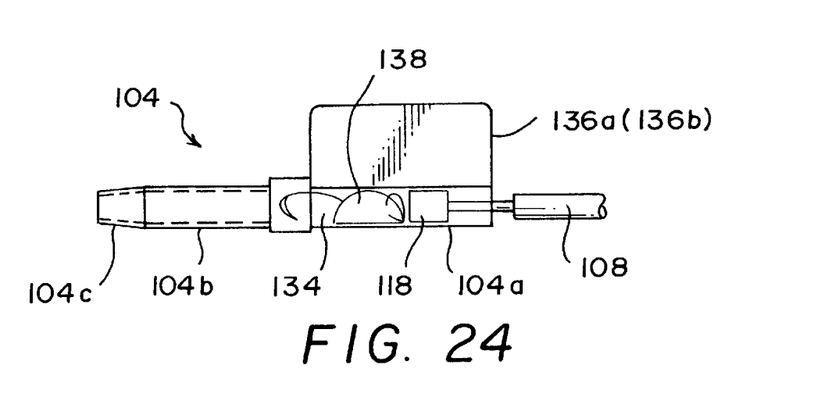
FIG. 24 is a side elevational view of a lens cartridge showing the plunger tip according to the present invention inside the delivery passageway through the lens cartridge in contact with a folded deformable intraocular lens.
Figures 25, 26:
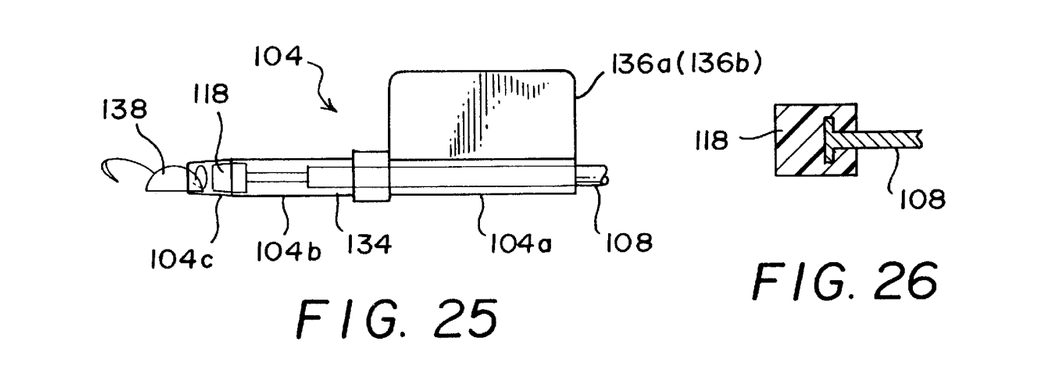
FIG. 25 is a side elevational view of a lens cartridge showing the plunger tip according to the present invention inside the delivery passageway through the lens cartridge forcing the folded deformable intraocular lens from the nozzle tip of the lens cartridge.
FIG. 26 is a detailed side longitudinal cross-sectional view of the deformable plunger tip of the multi-piece lens injecting apparatus shown in FIGS. 17–21, illustrating the connection between the deformable plunger tip and the end of the plunger.

The plunger 132 is then advanced forward so that the deformable plunger tip 118 enters one end of the delivery passageway 134, as shown in FIG. 23. The plunger tip 118 is further advanced into contact with the deformable intraocular lens 138 to begin the forcing and advancing of the deformable intraocular lens through the delivery passageway 134. The deformable plunger tip 118 begins to deform inwardly when entering the inwardly tapering portion of the delivery passageway 134 located in the nozzle tip 104c. Final advancement of the plunger tip 118 causes the deformable intraocular lens 138 to exit the nozzle tip 104c.

Figure 27:
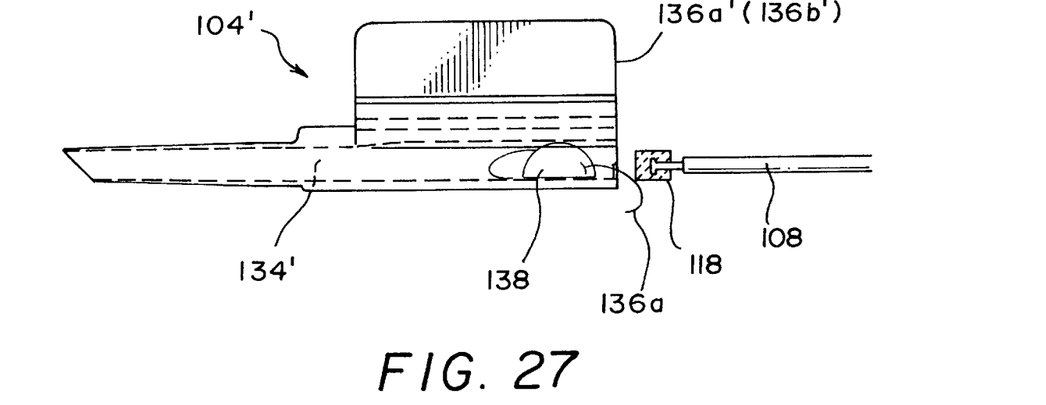
FIG. 27 is a side elevational view of another embodiment of a lens cartridge illustrating the loading of the plunger tip into the delivery passageway thereof.
Figure 28:
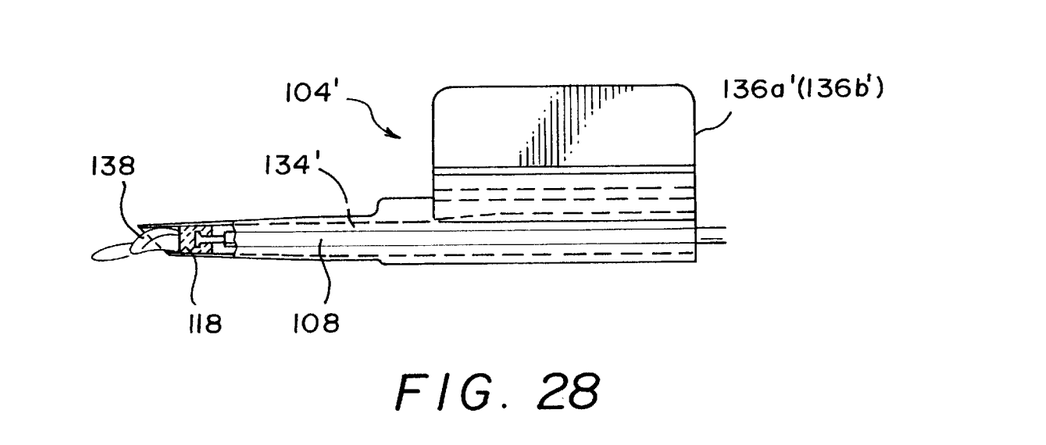
FIG. 28 is a side elevational view of the lens cartridge shown in FIG. 27, wherein the plunger tip has been advanced to the extent that the deformable intraocular lens is exiting the tip of the nozzle portion of the lens cartridge.

Another embodiment of the lens cartridge 104' is shown in FIGS. 27 and 28. The deformable intraocular lens is loaded into the delivery passageway 134' of the lens cartridge 104' with the trailing haptic 138a of the deformable intraocular lens 138 extending from the delivery passageway 134'. The deformable plunger tip 118 is pushed into the end of the delivery passageway 134' in a manner so that the trailing haptic 138a is not caught between the deformable plunger tip 118 and inner wall of the delivery passageway 134'. For example, the trailing haptic 138a is gently contacted by the end face of the deformable plunger tip 118 and manipulated (e.g. teased) therewith until the trailing haptic 138a is fully contained in the delivery passageway 134' before the deformable plunger tip 108 is forced into the end of the delivery passageway 134' to make contact with the optic portion of the deformable intraocular lens.

Figure 29:
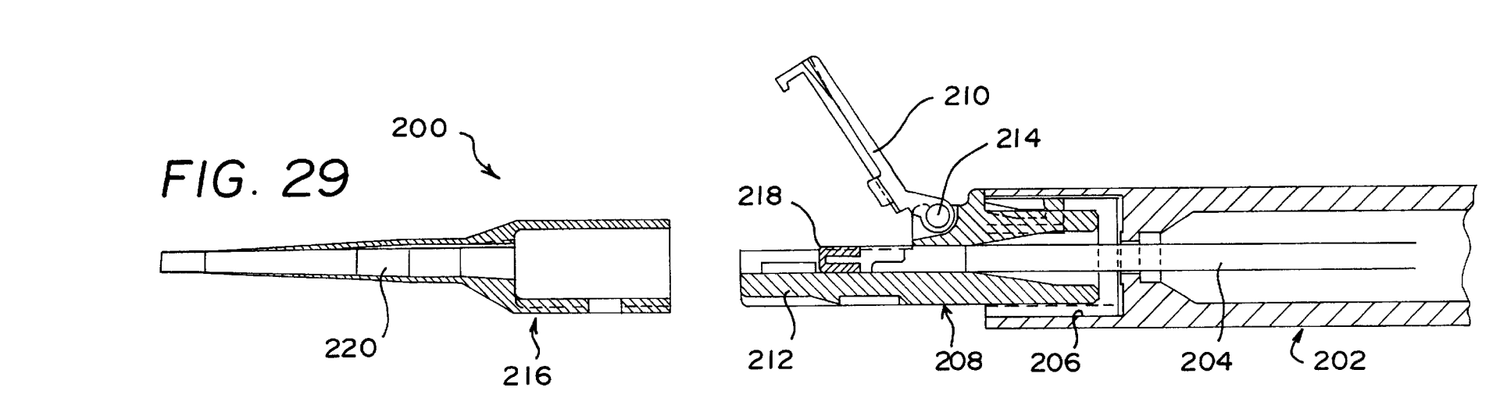
FIG. 29 is a broken away longitudinal cross-sectional view of a further embodiment of a deformable intraocular lens injecting apparatus partially disassembled, and including a transverse hinged lens cartridge in an opened condition for receiving a deformable intraocular lens.
Figure 30:
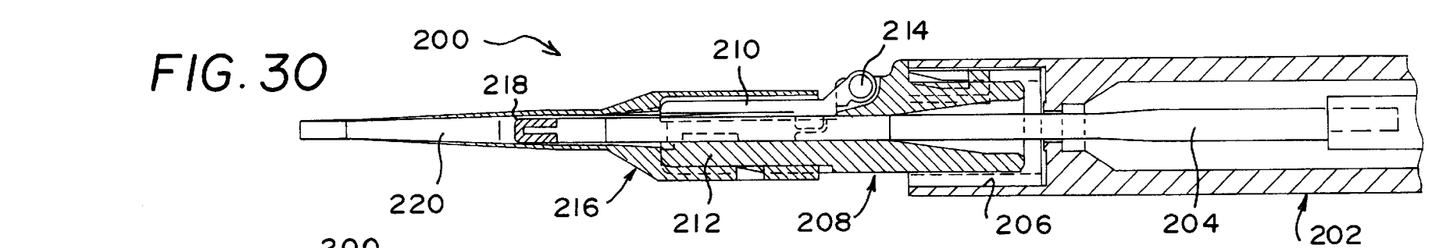
FIG. 30 is a broken way longitudinal cross-sectional view of the lens injecting apparatus shown in FIG. 29, however, with the lens cartridge is a closed condition.
Figure 31:
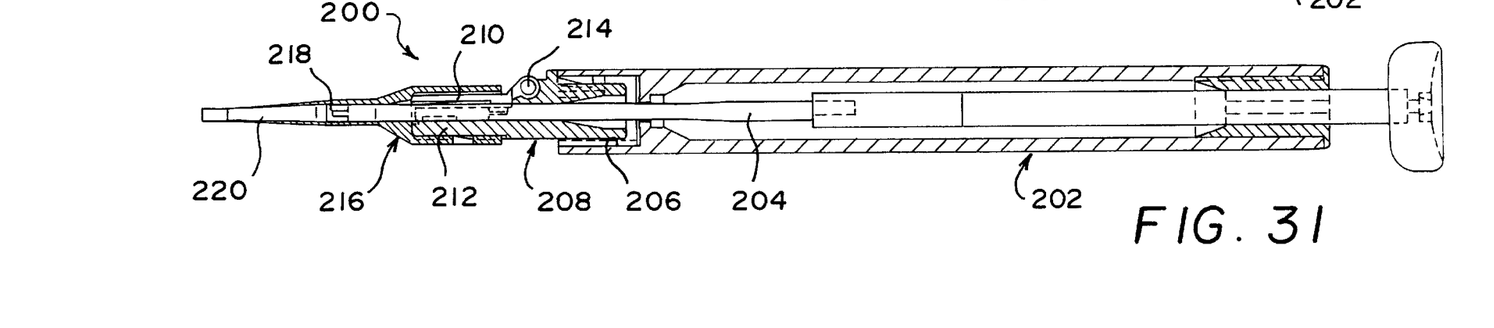
FIG. 31 is a longitudinal cross-sectional view of the lens injecting apparatus shown in FIG. 30.

A further embodiment of a deformable intraocular lens injecting apparatus 200 is shown in FIGS. 29–31. The lens injecting apparatus 200 comprises three (3) separate components including 1) a lens injecting device 202 containing a slidable plunger 204 and a lens cartridge receiver 206; 2) a transverse hinged lens cartridge 208 having an upper portion 210 and a lower portion 212 connected together by a transverse hinge 214; and 3) a nozzle portion 216.

The plunger 202 is provided with a deformable plunger tip 218 for cooperating with an inwardly tapering delivery passageway 220 extending through the lens cartridge 208 and nozzle portion 216.

We claim:

1. A deformable intraocular lens injecting apparatus, comprising:

a body portion having a lens delivery passageway configured for receiving a deformable intraocular lens;

a movable plunger disposed within said body portion, said plunger including a soft deformable tip for contacting with and advancing the deformable intraocular lens through said lens delivery passageway, said soft deformable tip being made of foam and configured to conform to the size and shape of said lens delivery passageway; and wherein said deformable tip is made of an expandable material that can absorb liquid and swell.

2. An apparatus according to claim 1, wherein said deformable tip is a separate piece connected to said plunger.

3. An apparatus according to claim 1, wherein said deformable tip is formed on said plunger.

4. An apparatus according to claim 1, wherein said lens delivery passageway is an inwardly tapering delivery passageway in a direction of lens delivery.

5. An apparatus according to claim 1, wherein said plunger tip is configured to be compressed when positioned within said lens delivery passageway.

6. An apparatus according to claim 1, wherein at least a portion of said plunger is made of deformable material to provide a deformable tip.

7. An apparatus according to claim 1, wherein said deformable plunger tip has a flat end face.

8. An apparatus according to claim 1, wherein said deformable plunger tip has a faceted tip configuration.

9. An apparatus according to claim 1, wherein said deformable plunger tip is made of a resiliently deformable material.

10. A deformable intraocular lens injecting apparatus, comprising:

a body portion having a lens delivery passageway configured for receiving a deformable intraocular lens;

a movable plunger disposed within said body portion, said plunger including a soft deformable tip for contacting with and advancing the deformable intraocular lens through said lens delivery passageway, said soft deformable tip being made of sponge and configured to conform to the size and shape of said lens delivery passageway; and wherein said deformable tip is made of an expandable material that can absorb liquid and swell.

11. An apparatus according to claim 10, wherein said deformable tip is a separate piece connected to said plunger.

12. An apparatus according to claim 10, wherein said deformable tip is formed on said plunger.

13. An apparatus according to claim 10, wherein said lens delivery passageway is an inwardly tapering delivery passageway in a direction of lens delivery.

14. An apparatus according to claim 10, wherein said plunger tip is configured to be compressed when positioned within said lens delivery passageway.

15. An apparatus according to claim 10, wherein at least a portion of said plunger is made of deformable material to provide a deformable tip.

16. An apparatus according to claim 10, wherein said deformable plunger tip has a flat end face.

17. An apparatus according to claim 10, wherein said deformable plunger tip has a faceted tip configuration.

18. An apparatus according to claim 10, wherein said deformable plunger tip is made of a resiliently deformable material.

* * * * *